(12) United States Patent
Engstrom et al.

(10) Patent No.: US 10,332,122 B1
(45) Date of Patent: Jun. 25, 2019

(54) OBTAINING AND ANALYZING USER PHYSIOLOGICAL DATA TO DETERMINE WHETHER A USER WOULD BENEFIT FROM USER SUPPORT

(71) Applicant: Intuit Inc., Mountain View, CA (US)

(72) Inventors: Garron Engstrom, San Diego, CA (US); Amir Eftekhari, San Diego, CA (US); Ann Catherine Jose, San Jose, CA (US); Erik Kaasila, Plaistow, NH (US); Konstantin Gizdarski, Cupertino, CA (US)

(73) Assignee: Intuit Inc., Mountain View, CA (US)

( * ) Notice: Subject to any disclaimer, the term of this patent is extended or adjusted under 35 U.S.C. 154(b) by 981 days.

(21) Appl. No.: 14/810,393

(22) Filed: Jul. 27, 2015

(51) Int. Cl.
| | |
|---|---|
| *G06Q 30/00* | (2012.01) |
| *A61B 5/16* | (2006.01) |
| *A61B 5/024* | (2006.01) |
| *H04L 12/58* | (2006.01) |

(52) U.S. Cl.
CPC ............ *G06Q 30/016* (2013.01); *A61B 5/024* (2013.01); *A61B 5/165* (2013.01); *H04L 51/04* (2013.01); *H04L 51/36* (2013.01)

(58) Field of Classification Search
CPC ....... A61B 5/00; A61B 5/0002; A61B 5/0004; A61B 5/0006; A61B 5/0008; A61B 5/0015; A61B 5/0017; A61B 5/0022; A61B 5/0024; A61B 5/0059; A61B 5/02; A61B 5/0205; A61B 5/024; A61B 5/02438
See application file for complete search history.

(56) References Cited

U.S. PATENT DOCUMENTS

| | | |
|---|---|---|
| 7,412,708 B1 | 8/2008 | Khan et al. |
| 8,683,348 B1 | 3/2014 | Blank et al. |
| 8,799,157 B1 | 8/2014 | Weisman et al. |
| 8,806,444 B1 | 8/2014 | Podgorny et al. |
| 8,903,176 B2 | 12/2014 | Hill |
| 9,098,109 B2 | 8/2015 | Lappalainen et al. |
| 9,330,239 B2 | 5/2016 | Koduri et al. |
| 9,444,824 B1 | 9/2016 | Balazs et al. |
| 9,785,534 B1 | 10/2017 | Paulus et al. |
| 9,930,102 B1 | 3/2018 | Paulus et al. |
| 2002/0199166 A1 | 12/2002 | Volcani et al. |
| 2003/0176798 A1* | 9/2003 | Simon ................. A61B 5/0006 600/509 |
| 2004/0066932 A1 | 4/2004 | Seligmann |
| 2005/0091487 A1 | 4/2005 | Cross et al. |
| 2006/0150243 A1 | 7/2006 | French et al. |
| 2006/0218506 A1 | 9/2006 | Srenger et al. |
| 2008/0276186 A1 | 11/2008 | Feduszczak et al. |
| 2009/0002178 A1 | 1/2009 | Guday et al. |
| 2009/0172100 A1 | 7/2009 | Callanan et al. |
| 2010/0083320 A1 | 4/2010 | Roberts et al. |

(Continued)

*Primary Examiner* — Alan Chen
(74) *Attorney, Agent, or Firm* — Hawley Troxell Ennis & Hawley LLP; Philip McKay

(57) ABSTRACT

A user's physiological status is monitored and the resulting physiological status data is obtained and analyzed to determine whether a user would benefit from user support intervention. If it is determined that the user would benefit from intervention, an intervention notification is provided to a user support service. The user support service may then provide dynamic and responsive user support. To provide effective, efficient user support, different types of user support can be provided to the user.

24 Claims, 3 Drawing Sheets

(56) References Cited

U.S. PATENT DOCUMENTS

| | | |
|---|---|---|
| 2010/0107075 A1 | 4/2010 | Hawthorne et al. |
| 2011/0131274 A1 | 6/2011 | Hille |
| 2012/0011477 A1 | 1/2012 | Sivadas |
| 2012/0059785 A1 | 3/2012 | Pascual et al. |
| 2012/0124456 A1 | 5/2012 | Perez et al. |
| 2012/0130819 A1 | 5/2012 | Willcock et al. |
| 2012/0270575 A1 | 10/2012 | Ferren et al. |
| 2012/0306643 A1 | 12/2012 | Dugan |
| 2013/0124496 A1 | 5/2013 | Edgar et al. |
| 2013/0152000 A1 | 6/2013 | Liu et al. |
| 2013/0159228 A1 | 6/2013 | Meijer et al. |
| 2013/0232207 A1 | 9/2013 | Westphal |
| 2013/0325948 A1 | 12/2013 | Chen et al. |
| 2014/0089399 A1 | 3/2014 | Chun et al. |
| 2014/0168279 A1 | 6/2014 | Huang |
| 2014/0221775 A1* | 8/2014 | Stivoric .............. G06Q 30/0242 600/301 |
| 2014/0289034 A1 | 9/2014 | Wu |
| 2014/0324749 A1 | 10/2014 | Peters et al. |
| 2014/0325379 A1 | 10/2014 | McDevitt et al. |
| 2015/0040026 A1 | 2/2015 | Sergunin |
| 2015/0046436 A1 | 2/2015 | Li et al. |
| 2015/0371516 A1 | 12/2015 | Petersen et al. |
| 2016/0000385 A1 | 1/2016 | Petersen et al. |
| 2016/0048274 A1 | 2/2016 | Rosenberg |
| 2016/0066829 A1 | 3/2016 | Sales et al. |
| 2017/0243055 A1 | 8/2017 | Naveh |
| 2017/0316707 A1 | 11/2017 | Lawrenson et al. |

* cited by examiner

OBTAINING AND ANALYZING USER PHYSIOLOGICAL DATA TO DETERMINE WHETHER A USER WOULD BENEFIT FROM USER SUPPORT

BACKGROUND

Customer service or user support services are integral aspects of product use. Consumers depend upon user support services to make effective use of a wide range of products and the ways in which user support is delivered are rapidly expanding. For example, a shopper visiting a retail clothing website may instant message with a user support provider to get additional information about the sizing of clothing or quality of fabric. Prior to the advent of remote user support services, a user would be required to consult with a user support provider in person. The user would thus be limited and potentially inconvenienced by the hours during which the support provider was available for consultation. Furthermore, the user might be required to travel to the professional's physical location. Beyond the inconveniences of scheduling and travel, the user would also be at the mercy of the support provider's ability to communicate effectively and identify the specific support the user needed. All of these factors limited a user's ability to receive meaningful support. Thus, these remote user support services have benefits that face-to-face interactions simply cannot provide because remote user support services do not have limited working hours and are not geographically limited.

Although remote user support services represent a potentially flexible, highly accessible, and affordable source of user support, they do have several significant shortcomings. For example, unlike human professionals providing support, many forms of remote user support services cannot detect, much less adjust to, a user's emotional state and intervene to provide additional or tailored support. Even though a user may be in a certain emotional state when using a product or may have certain responses to a product that change his or her emotional state, user support services are developed in such a way that the user must actually request support. Thus, traditional user support services are fairly passive in that they fail to respond to the specific or changing needs of a user, much less respond to variations in the emotional state of a given user. As a result, a currently available user support service can easily fail to provide responsive, appropriate support. This, in turn, may alienate a user from the product the user support service is attempting to support.

The inability of user support services to proactively intervene to provide support to a user results in users who are unable to take full advantage of the product they are using. Problematically, a user may not even realize that he or she needs support. Users who cannot fully reap the benefits of the product they are using often results in user frustration, and ultimately, in lost customers. This is because, predictably, when users are alienated from or become frustrated with product, they are far more likely to quit using it, which results in lost business.

For example, software systems offering tax return preparation services often present a static, predetermined, and pre-packaged user experience to all users as part of the tax return preparation interview process. These user experiences are typically presented to every user with little or no customization; are typically generated in a static and generic manner; and are typically provided via a combination of user experience components, which include, but are not limited to, interface displays, images, background music, and assistance resources. If a user becomes frustrated or confused with the presented user experience, the user may choose not to seek out, or may not even know about, the user support service supporting the tax return preparation service software system. In that case, the user may abandon the tax return preparation service even though the user support service may have been able to resolve any issue, and is provided for just that purpose.

As another example, if a user does reach out to user support and calls a user support phone number, the user may be routed to a random user support provider at a call center. The user support provider at the call center will likely have no information about the user's emotional state or any information about what specific aspects of the product is causing the user to reach out for help.

Given the consequences of dissatisfied customers, it is in a product provider's best interest to provide a responsive and proactive user support service. What is needed is a method and system for obtaining and analyzing user physiological data to determine whether a user would benefit from user support intervention.

SUMMARY

Embodiments of the present disclosure address some of the long-standing shortcomings associated with user support systems by defining types of user physiological data to be obtained and obtaining user physiological status data associated with a user. In one embodiment, user support events associated with providing service to a user are monitored and user support event data is generated. In one embodiment, the obtained user physiological status data and the known user support event data is analyzed and used to determine whether the user is reacting to a user support event and would benefit from a user support intervention.

In one embodiment, if it is determined that the user would benefit from intervention, an intervention notice is provided to the support provider. In one embodiment, after receiving the intervention notice, the support provider may implement one or more forms of intervention with the user. In various embodiments, the intervention serves to, for example, provide further explanation to the user, clarify information for the user, and/or provide assistance to the user.

The various embodiments of the disclosure and their associated benefits improve the technical fields of user support, communications, and data processing by ensuring that users quickly receive relevant support when necessary or desired. Therefore, implementations of embodiments of the present disclosure also represent a significant improvement to the field of user experience, particularly by allowing for the more efficient allocation of human and non-human resources. By determining whether a user would benefit from intervention, the present disclosure allows a support provider to offer relevant and efficient support to the user. Thus, if, for example, a user is confused about an instruction, the present disclosure provides the support provider with an intervention notice. In one embodiment, the support provider may then intervene, providing additional instruction to the confused user. By intervening, the support provider makes the user's experience more efficient, useful, and pleasant. Resource use is thereby maximized as a user who has a positive experience is less likely to abandon a product or process.

The disclosed embodiments do not encompass, embody, or preclude other forms of innovation in the areas of customer service, customer experience analysis, and user support. In addition, the disclosed embodiments are not related to any fundamental economic practice and, in fact, are directed to the relatively new technical area of remote user support and user support data collection. Consequently, the disclosed embodiments are not directed to, do not encompass, and are not merely abstract ideas or concepts.

In addition, as noted, the disclosed embodiments provide for significant improvements to the technical fields of customer service, user experience, and consumer analysis. Consequently, use of the disclosed embodiments results in more efficient use of human and non-human resources, potentially fewer processor cycles being utilized, potential reduced memory utilization, and potentially less communications bandwidth being utilized. As a result, computing systems and online services are transformed into faster, more efficient, and more effective computing systems and services by implementing the disclosed embodiments.

Figure 1:
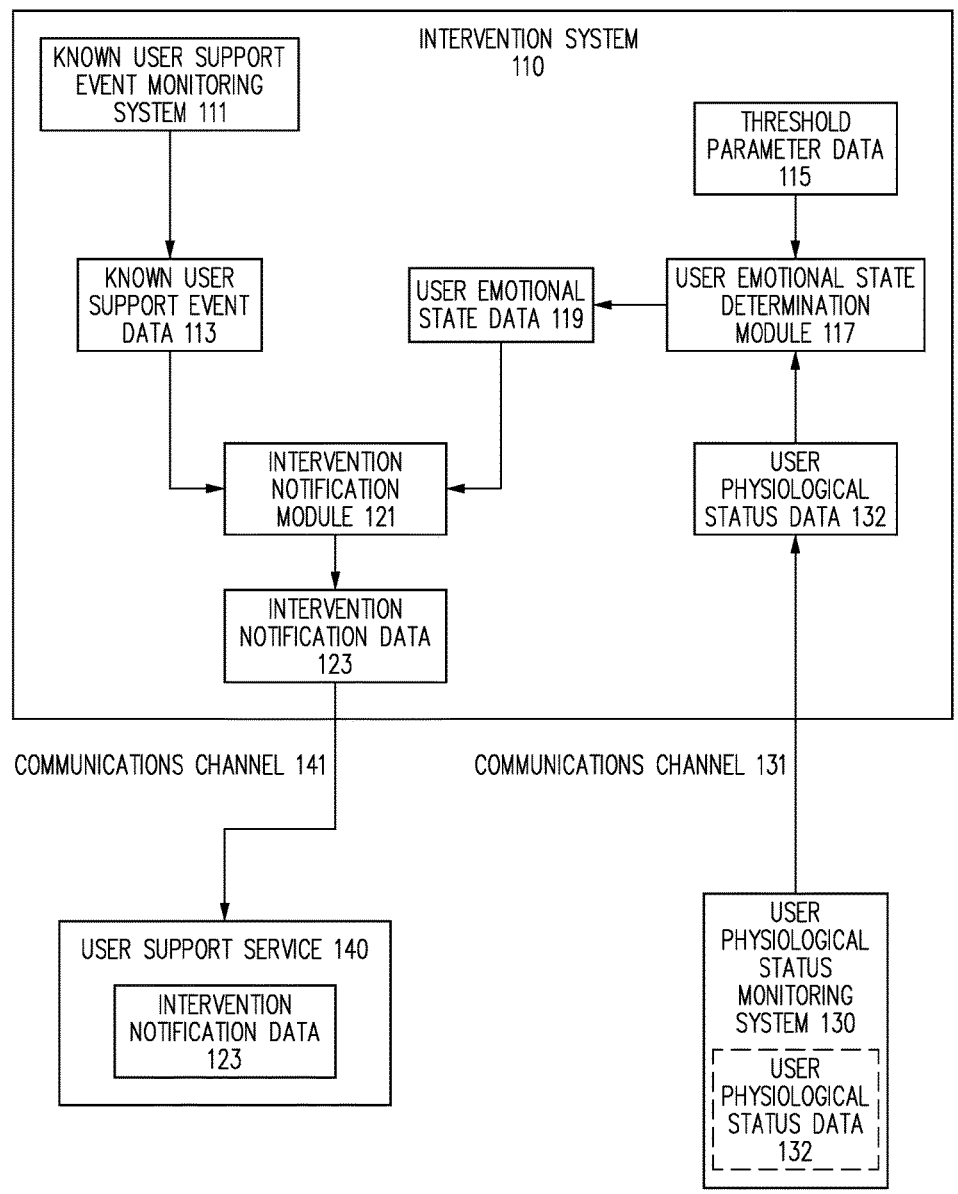
FIG. 1 is a block diagram of an architecture for analyzing user status data to determine whether a user would benefit from user support intervention, in accordance with one embodiment.

Common reference numerals are used throughout the FIG.s and the detailed description to indicate like elements. One skilled in the art will readily recognize that the above FIG.s are examples and that other architectures, modes of operation, orders of operation, and elements/functions can be provided and implemented without departing from the characteristics and features of the invention, as set forth in the claims.

TERM DEFINITIONS

As used herein, the terms "computing system," "computing device," and "computing entity," include, but are not limited to, the following: a virtual asset; a server computing system; a workstation; a desktop computing system; a mobile computing system, including, but not limited to, smart phones, cellular phones, portable devices, and/or devices worn or carried by a user; a database system or storage cluster; a switching system; a router; any hardware system; any communications system; any form of proxy system; a gateway system; a firewall system; a load balancing system; and/or any device, subsystem, or mechanism that includes components that can execute all, or part, of any one of the processes and/or operations as described herein.

In addition, as used herein, the terms "computing system," "computing device," and "computing entity," can denote, but are not limited to the following: systems made up of multiple virtual assets, server computing systems, workstations, desktop computing systems, mobile computing systems, database systems or storage clusters, switching systems, routers, hardware systems, communications systems, proxy systems, gateway systems, firewall systems, load balancing systems, and/or any devices that can be used to perform the processes and/or operations as described herein.

Herein, the terms "mobile computing system" and "mobile device" are used interchangeably and include, but are not limited to the following: a smart phone; a cellular phone; a digital wireless telephone; a tablet computing system; a notebook computing system; any portable computing system; a two-way pager; a Personal Digital Assistant (PDA); a media player; an Internet appliance; devices worn or carried by a user; or any other movable/mobile device and/or computing system that includes components that can execute all, or part, of any one of the processes and/or operations as described herein.

Herein, the term "production environment" includes the various components, or assets, used to deploy, implement, access, and use, a given application as that application is intended to be used. In various embodiments, production environments can include multiple assets that are combined, communicatively coupled, virtually and/or physically connected, and/or associated with one another, to provide the production environment implementing the application.

Herein, the term "software system" can be, but is not limited to, any data management system implemented on a computing system, accessed through one or more servers, accessed through a network, accessed through a cloud, and/or provided through any system or by any means, as discussed herein, and/or as known in the art at the time of filing, and/or as developed after the time of filing, that gathers/obtains data from one or more sources, provides data to one or more sources, and/or has the capability to analyze at least part of the data.

The term "software system" includes, but is not limited to, any software system that provides a product and/or user support service and is implemented on a computing system, accessed through one or more servers, accessed through a network, accessed through a cloud, and/or provided through any computing system or by any means as discussed herein, as known in the art at the time of filing, and/or as developed after the time of filing.

As used herein, the term "software system" includes, but is not limited to, the following: web-based, online, and/or computing system implemented personal and/or business tax preparation systems, services, packages, programs, modules, or applications; web-based, online, and/or computing system implemented personal and/or business financial management systems, services, packages, programs, modules, or applications; web-based, online, and/or computing system implemented personal and/or business management systems, services, packages, programs, modules, or applications; web-based, online, and/or computing system implemented personal and/or business accounting and/or invoicing systems, services, packages, programs, modules, or applications; and various other personal and/or business electronic data management systems, services, packages, programs, modules, or applications, whether known at the time of filling or as developed later.

Specific examples of software systems include, but are not limited to the following: TurboTax™ available from Intuit, Inc. of Mountain View, Calif.; TurboTax Online™ available from Intuit, Inc. of Mountain View, Calif.; Quicken™, available from Intuit, Inc. of Mountain View, Calif.; Quicken Online™, available from Intuit, Inc. of Mountain View, Calif.; QuickBooks™, available from Intuit, Inc. of Mountain View, Calif.; QuickBooks Online™, available from Intuit, Inc. of Mountain View, Calif.; Mint™, available from Intuit, Inc. of Mountain View, Calif.; Mint Online™, available from Intuit, Inc. of Mountain View, Calif.; and/or various other software systems discussed herein, and/or known to those of skill in the art at the time of filing, and/or as developed after the time of filing.

As specific illustrative examples, the assets making up a given production environment can include, but are not limited to, the following: one or more computing environments used to implement the application in the production environment such as a data center, a cloud computing environment, a dedicated hosting environment, and/or one or more other computing environments in which one or more assets used by the application in the production environment are implemented; one or more computing systems or computing entities used to implement the application in the production environment; one or more virtual assets used to implement the application in the production environment; one or more supervisory or control systems, such as hypervisors, or other monitoring and management systems used to monitor and control assets and/or components of the production environment; one or more communications channels for sending and receiving data used to implement the application in the production environment; one or more access control systems for limiting access to various components of the production environment, such as firewalls and gateways; one or more traffic and/or routing systems used to direct, control, and/or buffer data traffic to components of the production environment, such as routers and switches; one or more communications endpoint proxy systems used to buffer, process, and/or direct data traffic, such as load balancers or buffers; one or more secure communication protocols and/or endpoints used to encrypt/decrypt data, such as Secure Sockets Layer (SSL) protocols, used to implement the application in the production environment; one or more databases used to store data in the production environment; one or more internal or external services used to implement the application in the production environment; one or more backend systems, such as backend servers or other hardware used to process data and implement the application in the production environment; one or more software systems used to implement the application in the production environment; and/or any other virtual and/or physical assets/components making up an actual production environment in which an application is deployed, implemented, accessed, and run, e.g., operated, as discussed herein, and/or as known in the art at the time of filing, and/or as developed after the time of filing.

As used herein, the term "computing environment" includes, but is not limited to, a logical or physical grouping of connected or networked computing systems and/or virtual assets using the same infrastructure and systems such as, but not limited to, hardware systems, software systems, and networking/communications systems. Typically, computing environments are either known, "trusted" environments or unknown, "untrusted" environments. Typically, trusted computing environments are those where the assets, infrastructure, communication and networking systems, and security systems associated with the computing systems and/or virtual assets making up the trusted computing environment, are either under the control of, or known to, a party.

In various embodiments, each computing environment includes allocated assets and virtual assets associated with, and controlled or used to create, and/or deploy, and/or operate an application.

In various embodiments, one or more cloud computing environments are used to create, and/or deploy, and/or operate an application that can be any form of cloud computing environment, such as, but not limited to, a public cloud; a private cloud; a virtual private network (VPN); a subnet; a Virtual Private Cloud (VPC); a sub-net or any security/communications grouping; or any other cloud-based infrastructure, sub-structure, or architecture, as discussed herein, and/or as known in the art at the time of filing, and/or as developed after the time of filing.

In many cases, a given application, service, or intermediary service may utilize, and interface with, multiple cloud computing environments, such as multiple VPCs, in the course of being created, and/or deployed, and/or operated.

As used herein, the term "virtual asset" includes any virtualized entity or resource, and/or virtualized part of an actual, or "bare metal," entity. In various embodiments, the virtual assets can be, but are not limited to, the following: virtual machines, virtual servers, and instances implemented in a cloud computing environment; databases associated with a cloud computing environment, and/or implemented in a cloud computing environment; services associated with, and/or delivered through, a cloud computing environment; communications systems used with, part of, or provided through a cloud computing environment; and/or any other virtualized assets and/or sub-systems of "bare metal" physical devices such as mobile devices, remote sensors, laptops, desktops, point-of-sale devices, etc., located within a data center, within a cloud computing environment, and/or any other physical or logical location, as discussed herein, and/or as known/available in the art at the time of filing, and/or as developed/made available after the time of filing.

In various embodiments, any, or all, of the assets making up a given production environment discussed herein, and/or as known in the art at the time of filing, and/or as developed after the time of filing can be implemented as one or more virtual assets.

In one embodiment, two or more assets, such as computing systems and/or virtual assets, and/or two or more computing environments are connected by one or more communications channels including but not limited to, Secure Sockets Layer (SSL) communications channels and various other secure communications channels, and/or distributed computing system networks, such as, but not limited to the following: a public cloud; a private cloud; a virtual private network (VPN); a subnet; any general network, communications network, or general network/communications network system; a combination of different network types; a public network; a private network; a satellite network; a cable network; or any other network capable of allowing communication between two or more assets, computing systems, and/or virtual assets, as discussed herein, and/or available or known at the time of filing, and/or as developed after the time of filing.

As used herein, the term "network" includes, but is not limited to, any network or network system such as, but not limited to, the following: a peer-to-peer network; a hybrid peer-to-peer network; a Local Area Network (LAN); a Wide Area Network (WAN); a public network, such as the Internet; a private network; a cellular network; any general network, communications network, or general network/communications network system; a wireless network; a wired network; a wireless and wired combination network; a satellite network; a cable network; any combination of different network types; and/or any other system capable of allowing communication between two or more assets, virtual assets, and/or computing systems, whether available or known at the time of filing or as later developed.

Herein, the terms "user," "user consumer," and "customer" are used interchangeably to denote any party and/or entity that interfaces with, and/or with which information is exchanged, using the method and system for using physiological status data to determine whether a user would benefit from user support intervention described herein, and/or a person and/or entity that interfaces with, and/or with which information is exchanged, using the method and system for using physiological status data to determine whether a user would benefit from user support intervention described herein, and/or a legal guardian of person and/or entity that interfaces with, and/or with which information is exchanged, using the for using physiological status data to determine whether a user would benefit from user support intervention described herein, and/or an authorized agent of any party and/or person and/or entity that interfaces with, and/or with which information is exchanged, using the method and system for using physiological status data to determine whether a user would benefit from user support intervention described herein. For instance, in various embodiments, a user can be, but is not limited to, a person, a commercial entity, an application, a service, and/or a computing system.

Herein, the term "emotional state" refers to the emotional state of a user, which can include, but is not limited to, the following: a tense emotional state; a stressed emotional state; an upset emotional state; a frustrated emotional state; a nervous emotional state; a happy emotional state or happiness; a sad emotional state or sadness; a surprised emotional state or surprise; a fearful emotional state or fear; a disgusted emotional state or disgust; an angry emotional state or anger; a depressed emotional state; a bored emotional state; a fatigued emotional state; an alert emotional state; an excited emotional state; an elated emotional state; a contented emotional state; a serene emotional state; a relaxed emotional state; and/or a calm emotional state.

As used herein, in various embodiments, the term "user physiological status data" refers to a quantitative representation of physiological, behavioral, or experiential indications of a user's emotional state.

As used herein, the term "threshold parameter" refers to specific values and/or ranges of values associated with user physiological status data, or a quantitative representation or quantitative representations of physiological, behavioral, or experiential indications of a user's emotional state.

Herein, the term "user experience" includes the practical, experiential, affective, significant, and/or valuable aspects of human-software interaction.

Herein, the term "user support event" includes a user experience component. A user experience includes the practical, experiential, affective, significant, and/or valuable aspects of human-software interaction including, but not limited to, data entry, question submission, and/or interview process. As used herein, the term "user support event" includes a user experience component or components provided or displayed to the user and known to the user support service such as, but not limited to, the following: user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing.

Herein, the term "user support event" also includes a support provider-to-user interaction, e.g. a human-to-human interaction. User support includes a range of services offered to users of a product or products and is intended to help users effectively use the product or products. As used herein, the term "user support event" includes asking a question of a user, providing an answer to a user, corresponding with a user, speaking with a user, texting with a user, electronically chatting with a user, and/or registering a complaint from a user. A user support event may be implemented over a telephone, on live chat, and/or over electronic messages. For example, in one embodiment, the user support event includes a support provider asking a user a question. In one embodiment, the user support event includes a support provider providing an explanation to a user.

Herein the term "intervention" refers to an interaction between a support system and a user including any form of conveying information as discussed herein, and/or as known in the art at the time of filing, and/or as developed after the time of filing. In various embodiments, an intervention includes text, specific wording of text, audio, video, visual, or any other data and formats/forms of data used to convey information, and/or the mechanisms used to relay the specific wording or the text, audio, video, visual, or any other data and formats/forms of data used to convey information as discussed herein, and/or as known in the art at the time of filing, and/or as developed after the time of filing. Specific examples of interventions include the wording of text, audio, video, visual, or any other data arrangement/format used to convey information and the e-mails, video, audio, icons, pop-up displays etc. used to convey the information. As an even more specific example, interventions include not only specific wording, but also a specific tone and/or means of content delivery, e.g., as good news, bad news, happy/upbeat, unhappy/down beat, etc.

DETAILED DISCLOSURE

Embodiments will now be discussed with reference to the accompanying FIG.s, which depict one or more exemplary embodiments. Embodiments may be implemented in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

Remote user support services may, in one embodiment, include electronic or telephonic user support. As noted above, one major downfall of electronic and/or telephonic user support services is the inability of those services to identify when a user is in need of intervention. Instead, support providers offer support based on pre-determined algorithms or programs. In the case of human support providers, support is offered based on the support provider's best guess as to the user's emotions. By operating on generalities, however, these solutions fail to truly identify whether an individual user is in need of support.

Clearly, the situation described above is inefficient and inconvenient for both the support provider and the user. This, in and of itself, diminishes the usefulness of user support systems.

Embodiments of the present disclosure address some of the shortcomings associated with traditional user support systems by analyzing user physiological status data to determine if a user would benefit from intervention.

In one embodiment, one or more types of user physiological status data to be obtained and analyzed are defined. In one embodiment, the user physiological status data is historical user data representing the individual user's historical data and experiences related to the current user support event, and/or historical data and experiences related to the current user support event associated with peers of the user; and/or historical data and experiences related to the user support event associated with users similarly situated with the user. In one embodiment, the user physiological status data to be obtained and analyzed is current physiological status data associated with the user.

In various embodiments, the user physiological status data to be obtained and analyzed may include, but is not limited to, data associated with the user's pulse; data associated with the user's movement; the user's heart rate; the user's blood pressure; the speed with which the user is speaking; the cadence with which the user is speaking; the user's body temperature; whether the user is perspiring; the amount of perspiration present on the user's skin; the force with which the user touches hardware associated with a user physiological status monitoring system; the speed with which the user touches hardware associated with the user physiological status monitoring system; the user's facial expression; whether the user's eyebrows are raised; the shape of the user's eyebrows; whether the skin below the user's brow is stretched; the presence of wrinkles on the user's forehead; the location of wrinkles on the user's forehead; the extent to which the user's eyelids are opened; the extent to which the user's upper eyelid is opened; the extent to which the user's lower eyelid is opened; whether lines show below the user's lower eyelid; the amount of the white of the user's eye showing; the extent to which the user's jaw is open; whether the user's teeth are parted; whether the user's mouth is parted; whether the user's upper lip is raised; whether the user's lower lip is raised; the shape of the user's mouth; whether the user's nose is wrinkled; whether the user's nostrils are dilated; whether the user's cheeks are raised; whether the user's lower jaw juts out; the user's voice; the volume and frequency of the user's voice; and/or various other user physiological status data similar to the specific illustrative user data examples discussed herein, and/or known in the art at the time of filing, and/or as developed after the time of filing.

In one embodiment, threshold parameter data associated with each type of user physiological status data is identified and defined. In one embodiment, a specific threshold parameter data is defined for each type of user physiological status data to determine whether a user is in an emotional state such that the user would benefit from intervention. For example, a defined threshold parameter may provide that when a user's heart is beating at a rate greater than 100 beats per minute, the user is stressed and would benefit from intervention.

In one embodiment, the threshold parameter data associated with one or more of the one or more types of user physiological status data is identified and defined based on user physiological status data obtained from a group of people, and/or norms obtained from various medical data processors and/or medical institutions. In one embodiment, the threshold parameter data associated with one or more of the one or more types of user physiological status data is identified and defined based on user physiological status data obtained from the specific user, i.e. the threshold parameter data is customized to the specific, current user based on user historical physiological status data. For example, in one embodiment, a user's historical physiological status data may reveal that the user has a resting heart rate of over 100 beats per minute and that when the user's heart is beating at a rate of 110 beats per minute, the user is not stressed or in need of intervention. In some of these embodiments, the threshold parameter data associated with one of the one or more types of user physiological status data from a group of people and/or norms obtained from various medical data processors and medical institutions is initially used as base data and then a customized user physiological status profile for the specific user is developed based on feedback from the specific user and physiological status data monitoring of the specific user.

In one embodiment, threshold parameter data representing the defined threshold parameters for the defined one or more types of user physiological status data to be obtained and analyzed is generated.

In one embodiment, the threshold parameter data is stored in a partitioned threshold parameter data section of a memory device and/or system, such as any memory device and/or system discussed herein, and/or as known at the time of filing, and/or as developed after the time of filing.

In one embodiment, user support events associated with providing support to a user are identified. In one embodiment, a user support event includes a user experience component. A user experience includes the practical, experiential, affective, significant, and/or valuable aspects of human-software interaction including, but not limited to, data entry, question submission, and/or interview process. In one embodiment, a user support event includes a user experience component or components provided or displayed to the user and known to the user support service such as, but not limited to, the following: user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing.

In one embodiment, a user support event includes a support provider-to-user interaction, e.g. a human-to-human interaction. User support includes a range of services offered to users of a product or products and is intended to help users effectively use the product or products. In one embodiment, a user support event includes asking a question of a user, providing an answer to a user, corresponding with a user, speaking with a user, texting with a user, electronically chatting with a user, and/or registering a complaint from a user. A user support event may be implemented over a telephone, on live chat, and/or over electronic messages. For example, in one embodiment, the user support event includes a support provider asking a user a question. In one embodiment, the user support event includes a support provider providing an explanation to a user.

In one embodiment, one or more user support events associated with providing support to a user are monitored.

In one embodiment, user support event data is generated.

In one embodiment, user physiological status data associated with the user is obtained. In one embodiment, current, or relatively current, user physiological status data associated with the user is obtained. According to one embodiment, the user physiological status data associated with the user is obtained using one or more processes, systems, mechanisms, and/or means for obtaining user physiological status data, as discussed herein, as known in the art at the time of filing, and/or as developed after the time of filing.

As a specific illustrative example, in one embodiment, the user physiological status data is obtained using a user physiological status monitoring system. As another specific illustrative example, in one embodiment, the user physiological status data is obtained using a wearable device associated with a user physiological status monitoring system.

In one embodiment, the user physiological status data includes the user's pulse and is obtained using a heart rate monitor operatively coupled to, and/or otherwise associated with, a computing system used to implement at least part of the user physiological status monitoring system. In one embodiment, the user physiological status data includes the user's blood pressure and is obtained using a blood pressure monitor operatively coupled to, and/or otherwise associated with, a computing system used to implement at least part of the user physiological status monitoring system. In one embodiment, the user physiological status data includes the user's facial expression and is obtained using facial expression recognition software and/or hardware operatively coupled to, and/or otherwise associated with, a computing system used to implement at least part of the user physiological status monitoring system. In one embodiment, the user physiological status data includes the user's voice and is obtained using speech recognition software operatively coupled to, and/or otherwise associated with, a computing system used to implement at least part of the user physiological status monitoring system. In one embodiment, the user physiological status data includes the user's body temperature and is obtained using a temperature sensor operatively coupled to, and/or otherwise associated with, a computing system used to implement at least part of the user physiological status monitoring system. In one embodiment, the user physiological status data includes data measuring the user's perspiration and is obtained using a perspiration sensor operatively coupled to, and/or otherwise associated with, a computing system used to implement at least part of the user physiological status monitoring system. In one embodiment, the user physiological status data includes the force with which the user interacts with hardware associated with the user physiological status monitoring system and is obtained using a pressure sensor associated with a keyboard, and/or mouse, touch screen, and/or other user interface system operatively coupled to, and/or otherwise associated with, a computing system used to implement at least part of the user physiological status monitoring system. In one embodiment, the user physiological status data includes the speed with which the user interacts with hardware associated with the user physiological status monitoring system and is obtained using a sensor associated with a keyboard and/or mouse, touch screen, and/or other user interface system operatively coupled to, and/or otherwise associated with, a computing system used to implement at least part of the user physiological status monitoring system.

Numerous means, methods, systems, algorithms, procedures, and processes are known in the art for obtaining user physiological status data associated with a user. Consequently, a more detailed discussion of any particular means, method, system, algorithm, procedure, and process for obtaining user physiological status data associated with a user is omitted here to avoid detracting from the invention.

In one embodiment, it is determined whether the user would benefit from intervention. In one embodiment, intervention includes an interaction between a support system and a user including any form of conveying information as discussed herein, and/or as known in the art at the time of filing, and/or as developed after the time of filing. In various embodiments, an intervention includes text, specific wording of text, audio, video, visual, or any other data and formats/forms of data used to convey information, and/or the mechanisms used to relay the specific wording or the text, audio, video, visual, or any other data and formats/forms of data used to convey information as discussed herein, and/or as known in the art at the time of filing, and/or as developed after the time of filing. In various embodiments, interventions include the wording of text, audio, video, visual, or any other data arrangement/format used to convey information and the e-mails, video, audio, icons, pop-up displays etc. used to convey the information. In various embodiments, interventions include not only specific wording, but also a specific tone and/or means of content delivery, e.g., as good news, bad news, happy/upbeat, unhappy/down beat, etc.

In one embodiment, the determination as to whether the user would benefit from intervention depends upon the analysis of one or more of the known user support event data, threshold parameter data, and obtained user physiological status data. In various embodiments, the user physiological status data includes, but not limited to, the user's heart rate, the user's blood pressure, the volume of the user's voice, the speed with which the user is speaking, the frequency of the user voice, changes in the frequency of the user's voice, the cadence with which the user is speaking, the user's body temperature, whether the user is perspiring, the amount of perspiration present on the user's skin, the force with which the user interacts with hardware associated with the user physiological status monitoring system, the speed with which the user interacts with hardware associated with the user physiological status monitoring system, and/or various other user physiological status data similar to the specific illustrative user data examples discussed herein.

In one embodiment, the determination as to whether the user would benefit from intervention is based, at least in part, on analysis of user physiological status data such as, but not limited to, historical user data representing the individual user's historical data and experiences related to the current user support event being experienced by the user. In one embodiment, the determination as to whether the user would benefit from intervention is based on user physiological status data such as, but not limited to, data related to the current user support event being experienced by the user and associated with a segment of users having characteristics comparable to the user.

In one embodiment, the determination as to whether the user would benefit from intervention depends upon the user's emotional state, which is determined by generating emotional state data after comparing the threshold parameter data and the obtained user physiological status data. In one embodiment, the obtained user physiological status and threshold parameter data associated with the one or more types of user physiological status data are compared.

In one embodiment, based at least in part on the emotional state data resulting from the analysis of the obtained user physiological status data and the threshold parameter data associated with the one or more types of obtained user physiological status data, it is determined whether the user is in an emotional state such that the user would benefit from intervention.

The emotional state of a user can include, but is not limited to, the following: a stressed emotional state; an upset emotional state; a frustrated emotional state; a tense emotional state; a nervous emotional state; a happy emotional state or happiness; a sad emotional state or sadness; a surprised emotional state or surprise; a fearful emotional state or fear; a disgusted emotional state or disgust; an angry emotional state or anger; a depressed emotional state; a bored emotional state; a fatigued emotional state; an alert emotional state; an excited emotional state; an elated emotional state; a contented emotional state; a serene emotional state; a relaxed emotional state; and/or a calm emotional state.

For example, if the user's physiological status data shows that the user's heart is beating at a rate of 110 beats per minute and the defined threshold parameter data provides that when a user's heart is beating a rate greater than 100 beats per minute, the user is stressed, the user physiological status data and the threshold parameter data is analyzed and a determination is made that the user is in a stressed emotional state and would benefit from intervention.

In one embodiment, once an intervention is provided to the user, the user's physiological status data is monitored to determine whether the user would benefit from another intervention.

FIG. 1 is a block diagram of an architecture 100 for using user physiological status data to determine whether a user would benefit from user support intervention, in accordance with one embodiment.

As seen in FIG. 1, in one embodiment, an architecture 100 for using user physiological status data to determine whether a user would benefit from user support intervention, in accordance with one embodiment, includes INTERVENTION SYSTEM 110, USER PHYSIOLOGICAL STATUS MONITORING SYSTEM 130, and USER SUPPORT SERVICE 140. In various embodiments, INTERVENTION SYSTEM 110, USER PHYSIOLOGICAL STATUS MONITORING SYSTEM 130, and USER SUPPORT SERVICE 140 are communicatively coupled to one another with COMMUNICATIONS CHANNEL 131 and COMMUNICATIONS CHANNEL 141.

In one embodiment, communication channels 131 and 141 are any communications channels as discussed herein, as known in the art at the time of filing, and/or as developed after the time of filing. Those of skill in the art will readily recognize that in various embodiments, communication channels 131 and 141 can be the same communications channel or are implemented across two or more communications channels.

According to one embodiment, INTERVENTION SYSTEM 110 includes KNOWN USER SUPPORT EVENT MONITORING SYSTEM 111. According to one embodiment, KNOWN USER SUPPORT EVENT MONITORING SYSTEM 111 monitors support events associated with providing support to a user. In one embodiment, KNOWN USER SUPPORT EVENT MONITORING SYSTEM 111 generates KNOWN USER SUPPORT EVENT DATA 113.

In one embodiment, INTERVENTION SYSTEM 110 includes THRESHOLD PARAMETER DATA 115. In one embodiment, THRESHOLD PARAMETER DATA 115 represents specific values and/or ranges of values associated with user physiological status data, or a quantitative representation or quantitative representations of physiological, behavioral, or experiential indications of a user's emotional state.

In one embodiment, INTERVENTION SYSTEM 110 includes USER PHYSIOLOGICAL STATUS DATA 132.

In one embodiment, USER PHYSIOLOGICAL STATUS DATA 132 is obtained from USER PHYSIOLOGICAL STATUS MONITORING SYSTEM 130 via communications channel 131.

In one embodiment, USER EMOTIONAL STATE DETERMINATION MODULE 117 is used to analyze THRESHOLD PARAMETER DATA 115 and USER PHYSIOLOGICAL STATUS DATA 132. In one embodiment, USER EMOTIONAL STATE DETERMINATION MODULE 117 analyzes THRESHOLD PARAMETER DATA 115 and USER PHYSIOLOGICAL STATUS DATA 132 to determine the user's emotional state by, for example, using the user physiological status data to determine whether the user is confused or stressed.

In one embodiment USER EMOTIONAL STATE DETERMINATION MODULE 117 generates USER EMOTIONAL STATE DATA 119.

In one embodiment, INTERVENTION NOTIFICATION MODULE 121 analyzes USER EMOTIONAL STATE DATA 119 and KNOWN USER SUPPORT EVENT DATA 113 to determine whether the user would benefit from intervention.

In one embodiment, INTERVENTION NOTIFICATION MODULE 121 provides INTERVENTION NOTIFICATION DATA 123 to USER SUPPORT SERVICE 140. In one embodiment, if it is determined that the user would benefit from intervention, the user support service is provided with an intervention notification. In one embodiment, if it is determined that the user would not benefit from intervention, the user support service is provided with an intervention notification.

Those of skill in the art will readily recognize that in various embodiments, USER PHYSIOLOGICAL STATUS MONITORING SYSTEM 130, USER SUPPORT SERVICE 140, and INTERVENTION SYSTEM 110 can be the same system or are implemented across two or more systems.

The various embodiments of the disclosure and their associated benefits improve the technical fields of customer service, communications, and data processing by ensuring that users who need support are provided with an intervention. Therefore, implementations of embodiments of the present disclosure also represent a significant improvement to the field of user experience, particularly by allowing for the more efficient allocation of human and non-human resources. For example, by providing intervention to those users in need of additional support, users are not bothered with unnecessary support, but receive help when needed and appropriate.

As a result, using implementations of embodiments of the present disclosure, the fields of customer support, communications, and data processing are significantly improved. Consequently, this disclosure is not directed to simply an abstract idea and the embodiments of the present disclosure represent significantly more than any abstract idea related to the embodiments of the present disclosure.

Figure 2:
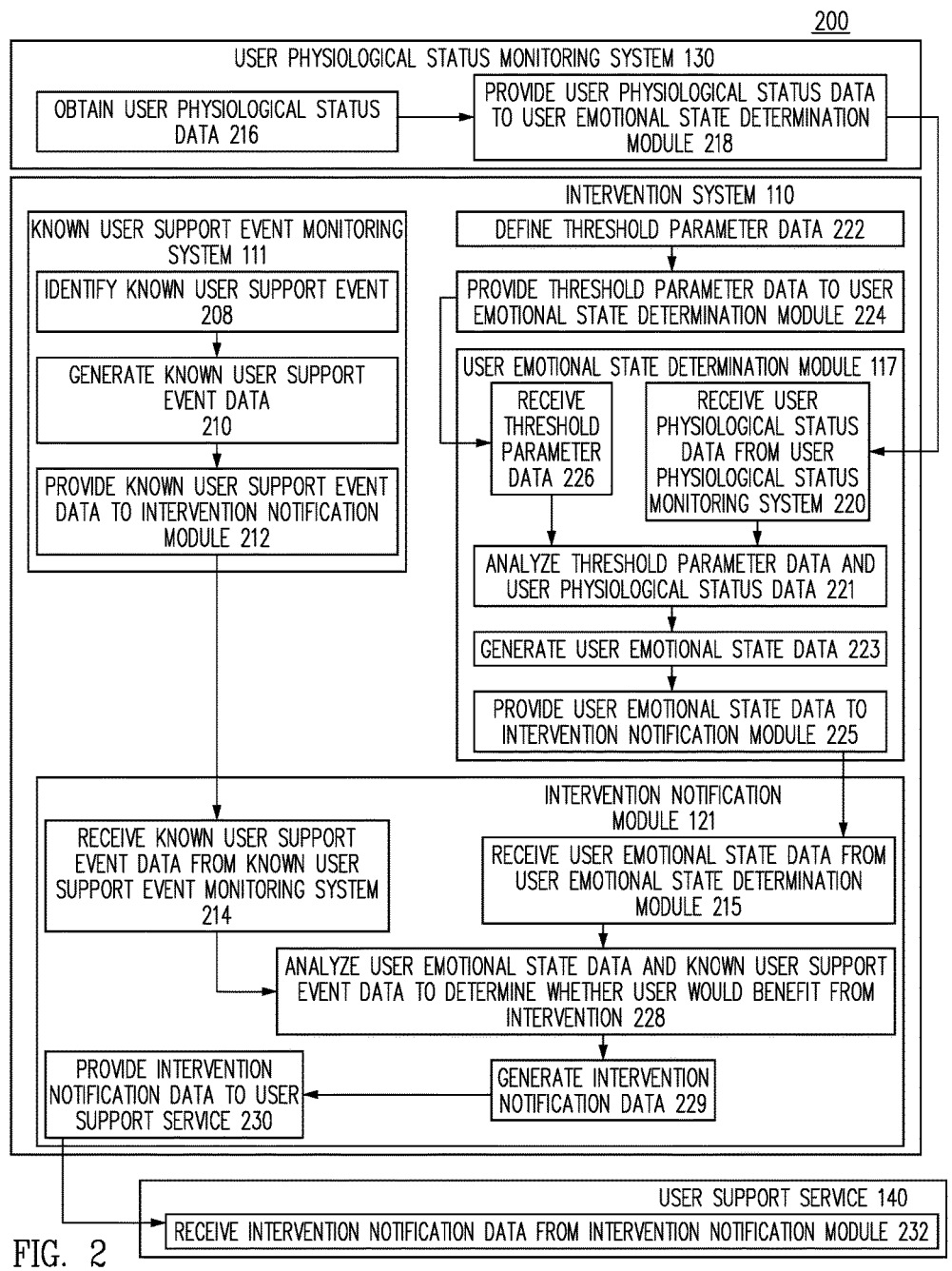
FIG. 2 is a block diagram of a process for analyzing user status data to determine whether a user would benefit from user support intervention, in accordance with one embodiment.

FIG. 2 illustrates a block diagram of a process 200 for using user physiological status data to determine whether a user would benefit from intervention, in accordance with one embodiment. Although a particular sequence of events is described, more or less events in various combinations may be included in process 200, according to various embodiments.

In one embodiment, INTERVENTION SYSTEM 110 defines threshold parameter data at DEFINE THRESHOLD PARAMETER DATA 222. In one embodiment, the threshold parameter data of DEFINE THRESHOLD PARAMETER DATA 222 is provided to USER EMOTIONAL STATE DETERMINATION MODULE 117 at PROVIDE THRESHOLD PARAMETER DATA TO USER EMOTIONAL STATE DETERMINATION MODULE 224.

In one embodiment, USER EMOTIONAL STATE DETERMINATION MODULE 117 receives threshold parameter data at RECEIVE THRESHOLD PARAMETER DATA 226.

In one embodiment, the user physiological status data is historical user data representing the individual user's historical data and experiences related to the known user support event data, and/or historical data and experiences related to the known user support event data associated with peers of the user; and/or historical data and experiences related to known user support event data associated with users similarly situated with the user. In one embodiment, the user physiological status data to be obtained and analyzed is current physiological status data associated with the user.

In various embodiments, the user physiological status data to be obtained and analyzed may include, but is not limited to, data associated with the user's pulse; data associated with the user's movement; the user's heart rate; the user's blood pressure; the speed with which the user is speaking; the cadence with which the user is speaking; the user's body temperature; whether the user is perspiring; the amount of perspiration present on the user's skin; the force with which the user touches hardware associated with a user physiological status monitoring system; the speed with which the user touches hardware associated with the user physiological status monitoring system; the user's facial expression; whether the user's eyebrows are raised; the shape of the user's eyebrows; whether the skin below the user's brow is stretched; the presence of wrinkles on the user's forehead; the location of wrinkles on the user's forehead; the extent to which the user's eyelids are opened; the extent to which the user's upper eyelid is opened; the extent to which the user's lower eyelid is opened; whether lines show below the user's lower eyelid; the amount of the white of the user's eye showing; the extent to which the user's jaw is open; whether the user's teeth are parted; whether the user's mouth is parted; whether the user's upper lip is raised; whether the user's lower lip is raised; the shape of the user's mouth; whether the user's nose is wrinkled; whether the user's nostrils are dilated; whether the user's cheeks are raised; whether the user's lower jaw juts out; the user's voice; the volume and frequency of the user's voice; and/or various other user physiological status data similar to the specific illustrative user data examples discussed herein, and/or known in the art at the time of filing, and/or as developed after the time of filing.

In one embodiment, user physiological status data is obtained via USER PHYSIOLOGICAL STATUS MONITORING SYSTEM 130 at OBTAIN USER PHYSIOLOGICAL STATUS DATA 216. In one embodiment, the user physiological status data includes the user's pulse and is obtained using a heart rate monitor operatively coupled to, and/or otherwise associated with, a computing system used to implement at least part of the user physiological status monitoring system. In one embodiment, the user physiological status data includes the user's blood pressure and is obtained using a blood pressure monitor operatively coupled to, and/or otherwise associated with, a computing system used to implement at least part of the user physiological status monitoring system. In one embodiment, the user physiological status data includes the user's facial expression and is obtained using facial expression recognition software and/or hardware operatively coupled to, and/or otherwise associated with, a computing system used to implement at least part of the user physiological status monitoring system. In one embodiment, the user physiological status data includes the user's voice and is obtained using speech recognition software operatively coupled to, and/or otherwise associated with, a computing system used to implement at least part of the user physiological status monitoring system. In one embodiment, the user physiological status data includes the user's body temperature and is obtained using a temperature sensor operatively coupled to, and/or otherwise associated with, a computing system used to implement at least part of the user physiological status monitoring system. In one embodiment, the user physiological status data includes data measuring the user's perspiration and is obtained using a perspiration sensor operatively coupled to, and/or otherwise associated with, a computing system used to implement at least part of the user physiological status monitoring system. In one embodiment, the user physiological status data includes the force with which the user interacts with hardware associated with the user physiological status monitoring system and is obtained using a pressure sensor associated with a keyboard, and/or mouse, touch screen, and/or other user interface system operatively coupled to, and/or otherwise associated with, a computing system used to implement at least part of the user physiological status monitoring system. In one embodiment, the user physiological status data includes the speed with which the user interacts with hardware associated with the user physiological status monitoring system and is obtained using a sensor associated with a keyboard and/or mouse, touch screen, and/or other user interface system operatively coupled to, and/or otherwise associated with, a computing system used to implement at least part of the user physiological status monitoring system.

In one embodiment, USER PHYSIOLOGICAL STATUS MONITORING SYSTEM 130 provides the user physiological status data of OBTAIN USER PHYSIOLOGICAL STATUS DATA 216 to USER EMOTIONAL STATE DETERMINATION MODULE 117 at PROVIDE USER PHYSIOLOGICAL STATUS DATA TO USER EMOTIONAL STATE DETERMINATION MODULE 218.

In one embodiment, USER EMOTIONAL STATE DETERMINATION MODULE 117 receives user physiological status data from USER PHYSIOLOGICAL STATUS MONITORING SYSTEM 130 at RECEIVE USER PHYSIOLOGICAL STATUS DATA FROM USER PHYSIOLOGICAL STATUS MONITORING SYSTEM 220.

In one embodiment, USER EMOTIONAL STATE DETERMINATION MODULE 117 analyzes the received threshold parameter data and user physiological status data at ANALYZE THRESHOLD PARAMETER DATA AND USER PHYSIOLOGICAL STATUS DATA 221.

In one embodiment, after analyzing the received threshold parameter data and user physiological status data at ANALYZE THRESHOLD PARAMETER DATA AND USER PHYSIOLOGICAL STATUS DATA 221, USER EMOTIONAL STATE DETERMINATION MODULE 117 generates user emotional state data at GENERATE USER EMOTIONAL STATE DATA 223.

In one embodiment, after generating emotional state data, USER EMOTIONAL STATE DETERMINATION MODULE 117 provides user emotional state data to INTERVENTION NOTIFICATION MODULE 121 at PROVIDE USER EMOTIONAL STATE DATA TO INTERVENTION NOTIFICATION MODULE 225.

In one embodiment, KNOWN USER SUPPORT EVENT MONITORING SYSTEM 111 identifies known user support events at IDENTIFY KNOWN USER SUPPORT EVENTS 208. In one embodiment, KNOWN USER SUPPORT EVENT MONITORING SYSTEM 111 generates known user support events data at GENERATE KNOWN USER SUPPORT EVENT DATA 210.

In one embodiment, KNOWN USER SUPPORT EVENT MONITORING SYSTEM 111 provides the known user support event data of GENERATE KNOWN USER SUPPORT EVENT DATA 210 to INTERVENTION NOTIFI- CATION MODULE 121 at PROVIDE KNOWN USER SUPPORT EVENT DATA TO INTERVENTION NOTIFICATION MODULE 212.

In one embodiment, INTERVENTION NOTIFICATION MODULE 121 receives the user emotional state data of GENERATE USER EMOTIONAL STATE DATA 223 at RECEIVE USER EMOTIONAL STATE DATA FROM USER EMOTIONAL STATE DETERMINATION MODULE 215.

In one embodiment, INTERVENTION NOTIFICATION MODULE 121 receives the known user support event data of GENERATE KNOWN USER SUPPORT EVENT DATA 210 at RECEIVE KNOWN USER SUPPORT EVENT DATA FROM KNOWN USER SUPPORT EVENTS MONITORING SYSTEM 214.

In one embodiment, INTERVENTION NOTIFICATION MODULE 121 analyzes the user emotional state data and the known user support event data at ANALYZE USER EMOTIONAL STATE DATA AND KNOWN USER SUPPORT EVENT DATA TO DETERMINE WHETHER USER WOULD BENEFIT FROM INTERVENTION 228 to determine whether the user would benefit from intervention.

In one embodiment, INTERVENTION NOTIFICATION MODULE 121 generates intervention notification data at GENERATE INTERVENTION NOTIFICATION DATA 229.

In one embodiment, INTERVENTION NOTIFICATION MODULE 121 provides the intervention notification data of GENERATE INTERVENTION NOTIFICATION DATA 229 to USER SUPPORT SERVICE 140 at PROVIDE INTERVENTION NOTIFICATION DATA TO USER SUPPORT SERVICE 230.

In one embodiment, USER SUPPORT SERVICE 140 receives the intervention notification data at RECEIVE INTERVENTION NOTIFICATION DATA FROM INTERVENTION NOTIFICATION MODULE 232.

The various embodiments of the disclosure and their associated benefits improve the technical fields of customer service, communications, and data processing by ensuring that those users in need of assistance receive timely and relevant user support. Therefore, implementations of embodiments of the present disclosure also represent a significant improvement to the field of user experience, particularly by allowing for the more efficient allocation of human and non-human resources. For example, by providing clarification to a user as the user becomes confused or providing assistance to the user as the user becomes frustrated, user support is offered in an efficient and effective manner.

In addition, by providing a user support intervention to only those users in need of support, the disclosed embodiments provide for fewer processor cycles being utilized, reduced memory utilization, and less communications bandwidth being utilized to relay data to and from user computing systems. As a result, computing systems are transformed into faster, more efficient and more effective computing systems by implementing the embodiments disclosed herein.

As a result, using implementations of embodiments of the present disclosure, the fields of user experience, customer service, and data processing are significantly improved.

Process

According to one embodiment of a process for using physiological status data to determine whether a user would benefit from user support intervention, known user support events are monitored. In one embodiment, user physiological status data is obtained and analyzed to determine whether the user is in an emotional state such that the user would benefit from user support intervention. For example, in one embodiment, the user physiological status data is used to determine whether the user is confused or irritated by the known user support event. Then, in one embodiment, if it is determined that the user would benefit from intervention, an intervention notice is provided to the user support service.

In one embodiment, if it is determined that the user would benefit from intervention and an intervention notice is provided to the user support service, known user support events are monitored relatively continually and user physiological status data is relatively continually obtained until it is determined that the user would not benefit from intervention.

In one embodiment, after it is determined that the user would not benefit from intervention, known user support events are monitored relatively continually and user physiological status data is relatively continually obtained to continue determining whether the user would benefit from intervention.

Figure 3:
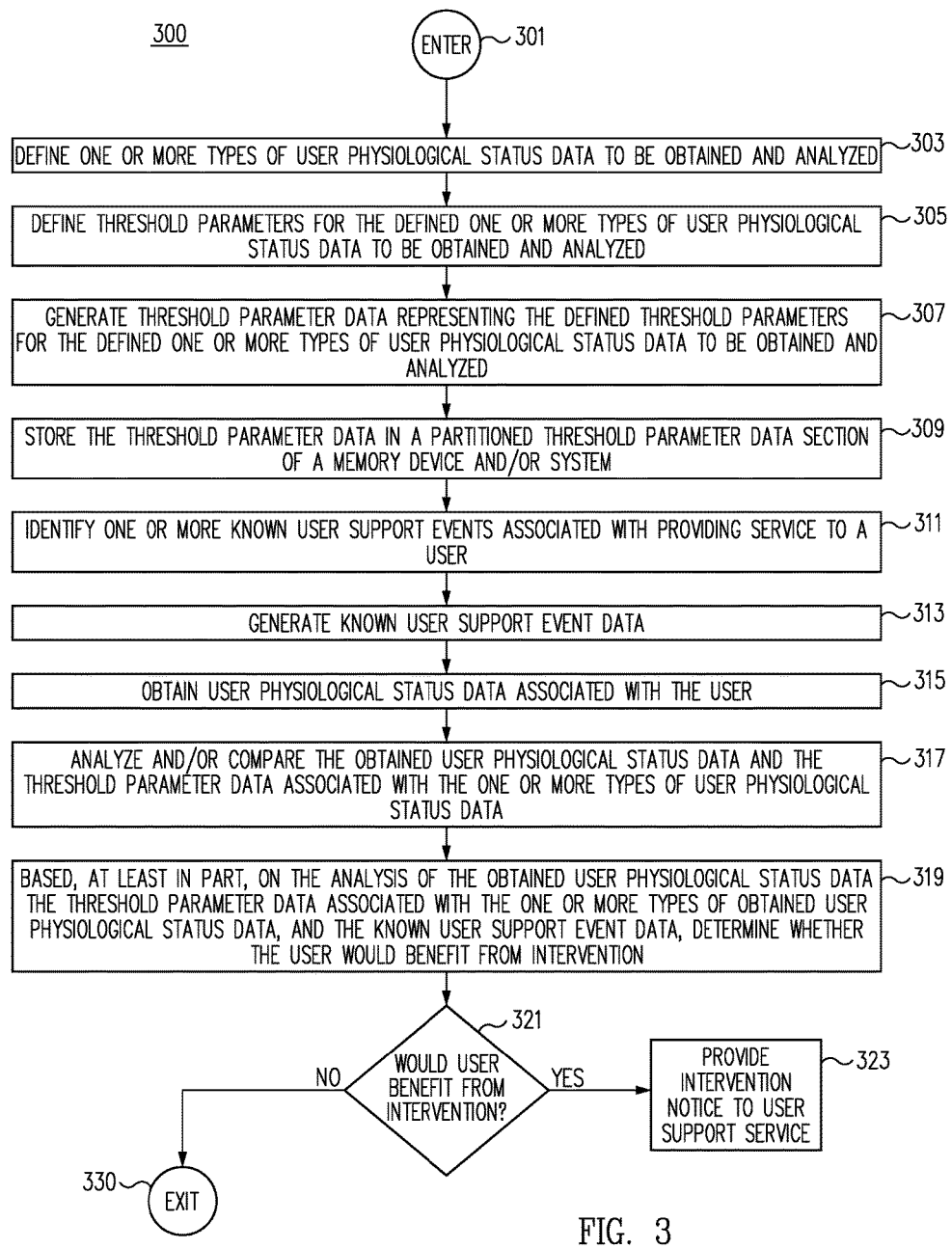
FIG. 3 is a flow diagram for analyzing user status data to determine whether a user would benefit from user support intervention, in accordance with one embodiment.

FIG. 3 is a flow diagram of a process 300 for using user physiological status data to determine whether a user would benefit from user support intervention, in accordance with one embodiment.

As seen in FIG. 3, process 300 for using user physiological status data to determine whether a user would benefit from user support intervention begins at ENTER OPERATION 301 and process flow proceeds to DEFINE ONE OR MORE TYPES OF USER PHYSIOLOGICAL STATUS DATA TO BE OBTAINED AND ANALYZED OPERATION 303.

In one embodiment, at DEFINE ONE OR MORE TYPES OF USER PHYSIOLOGICAL STATUS DATA TO BE OBTAINED AND ANALYZED OPERATION 303, user physiological status data is a quantitative representation of physiological, behavioral, or experiential indications of a user's emotional state.

In one embodiment, the user physiological status data of DEFINE ONE OR MORE TYPES OF USER PHYSIOLOGICAL STATUS DATA TO BE OBTAINED AND ANALYZED OPERATION 303 is historical user data representing the individual user's historical data and experiences related to the current user support event, and/or historical data and experiences related to the current user support event associated with peers of the user; and/or historical data and experiences related to the current support event associated with users similarly situated with the user. In one embodiment, the user physiological status data of DEFINE ONE OR MORE TYPES OF USER PHYSIOLOGICAL STATUS DATA TO BE OBTAINED AND ANALYZED OPERATION 303 is current physiological status data associated with the user.

In various embodiments, the user physiological status data of DEFINE ONE OR MORE TYPES OF USER PHYSIOLOGICAL STATUS DATA TO BE OBTAINED AND ANALYZED OPERATION 303 may include, but is not limited to, data associated with the user's pulse; data associated with the user's movement; the user's heart rate; the user's blood pressure; the speed with which the user is speaking; the cadence with which the user is speaking; the user's body temperature; whether the user is perspiring; the amount of perspiration present on the user's skin; the force with which the user touches hardware associated with a user physiological status monitoring system; the speed with which the user touches hardware associated with the user physiological status monitoring system; the user's facial expression; whether the user's eyebrows are raised; the shape of the user's eyebrows; whether the skin below the user's brow is stretched; the presence of wrinkles on the user's forehead; the location of wrinkles on the user's forehead; the extent to which the user's eyelids are opened; the extent to which the user's upper eyelid is opened; the extent to which the user's lower eyelid is opened; whether lines show below the user's lower eyelid; the amount of the white of the user's eye showing; the extent to which the user's jaw is open; whether the user's teeth are parted; whether the user's mouth is parted; whether the user's upper lip is raised; whether the user's lower lip is raised; the shape of the user's mouth; whether the user's nose is wrinkled; whether the user's nostrils are dilated; whether the user's cheeks are raised; whether the user's lower jaw juts out; the user's voice; the volume and frequency of the user's voice; and/or various other user physiological status data similar to the specific illustrative user data examples discussed herein, and/or known in the art at the time of filing, and/or as developed after the time of filing.

In one embodiment, once one or more types of user physiological status data to be obtained and analyzed are defined at DEFINE ONE OR MORE TYPES OF USER PHYSIOLOGICAL STATUS DATA TO BE OBTAINED AND ANALYZED OPERATION 303, process flow proceeds to DEFINE THRESHOLD PARAMETERS FOR THE DEFINED ONE OR MORE TYPES OF USER PHYSIOLOGICAL STATUS DATA TO BE OBTAINED AND ANALYZED OPERATION 305.

In one embodiment, at DEFINE THRESHOLD PARAMETERS FOR THE DEFINED ONE OR MORE TYPES OF USER PHYSIOLOGICAL STATUS DATA TO BE OBTAINED AND ANALYZED OPERATION 305, threshold parameters are defined for each type of user physiological status data to determine whether the user would benefit from intervention. For example, a defined threshold parameter may provide that when a user's heart is beating at a rate greater than 100 beats per minute, the user would benefit from intervention.

In one embodiment, at DEFINE THRESHOLD PARAMETERS FOR THE DEFINED ONE OR MORE TYPES OF USER PHYSIOLOGICAL STATUS DATA TO BE OBTAINED AND ANALYZED OPERATION 305, threshold parameters associated with one or more of the one or more types of user physiological status data is identified and defined based on user physiological status data obtained from a group of people, and/or norms obtained from various medical data processors and/or medical institutions. In one embodiment, at DEFINE THRESHOLD PARAMETERS FOR THE DEFINED ONE OR MORE TYPES OF USER PHYSIOLOGICAL STATUS DATA TO BE OBTAINED AND ANALYZED OPERATION 305, threshold parameters associated with one or more of the one or more types of user physiological status data is identified and defined based on user physiological status data obtained from the specific user, i.e. the threshold parameters are customized to the specific, current user based on user historical physiological status data. In some of these embodiments, the threshold parameters associated with one of the one or more types of user physiological status data from a group of people and/or norms obtained from various medical data processors and medical institutions is initially used as base data and then a customized user physiological status profile for the specific user is developed based on feedback from the specific user and physiological status data monitoring of the specific user.

In one embodiment, once threshold parameters for the defined one or more types of user physiological status data to be obtained and analyzed are defined at DEFINE THRESHOLD PARAMETERS FOR THE DEFINED ONE OR MORE TYPES OF USER PHYSIOLOGICAL STATUS DATA TO BE OBTAINED AND ANALYZED OPERATION 305, process flow proceeds to GENERATE THRESHOLD PARAMETER DATA REPRESENTING THE DEFINED THRESHOLD PARAMETERS FOR THE DEFINED ONE OR MORE TYPES OF USER PHYSIOLOGICAL STATUS DATA TO BE OBTAINED AND ANALYZED OPERATION 307.

In one embodiment, at GENERATE THRESHOLD PARAMETER DATA REPRESENTING THE DEFINED THRESHOLD PARAMETERS FOR THE DEFINED ONE OR MORE TYPES OF USER PHYSIOLOGICAL STATUS DATA TO BE OBTAINED AND ANALYZED OPERATION 307, threshold parameter data representing the defined threshold parameters for the defined one or more types of user physiological status data to be obtained and analyzed is generated.

In one embodiment, the threshold parameter data of GENERATE THRESHOLD PARAMETER DATA REPRESENTING THE DEFINED THRESHOLD PARAMETERS FOR THE DEFINED ONE OR MORE TYPES OF USER PHYSIOLOGICAL STATUS DATA TO BE OBTAINED AND ANALYZED OPERATION 307 is machine-readable representations of the defined threshold parameters.

In one embodiment, once threshold parameter data representing the defined threshold parameters for the defined one or more types of user physiological status data to be obtained and analyzed is generated at GENERATE THRESHOLD PARAMETER DATA REPRESENTING THE DEFINED THRESHOLD PARAMETERS FOR THE DEFINED ONE OR MORE TYPES OF USER PHYSIOLOGICAL STATUS DATA TO BE OBTAINED AND ANALYZED OPERATION 307, process flow proceeds to STORE THE THRESHOLD PARAMETER DATA IN A PARTITIONED THRESHOLD PARAMETER DATA SECTION OF A MEMORY DEVICE AND/OR SYSTEM OPERATION 309.

In one embodiment, at STORE THE THRESHOLD PARAMETER DATA IN A PARTITIONED THRESHOLD PARAMETER DATA SECTION OF A MEMORY DEVICE AND/OR SYSTEM OPERATION 309, the threshold parameter data is stored in a partitioned threshold parameter data section of a memory device and/or system.

In one embodiment, once the threshold parameter data is stored in a partitioned threshold parameter data section of a memory device and/or system at STORE THE THRESHOLD PARAMETER DATA IN A PARTITIONED THRESHOLD PARAMETER DATA SECTION OF A MEMORY DEVICE AND/OR SYSTEM OPERATION 309, process flow proceeds to IDENTIFY ONE OR MORE KNOWN USER SUPPORT EVENTS ASSOCIATED WITH PROVIDING SERVICE TO A USER OPERATION 311.

In one embodiment, known user support events are identified at IDENTIFY ONE OR MORE KNOWN USER SUPPORT EVENTS ASSOCIATED WITH PROVIDING SERVICE TO A USER OPERATION 311. In one embodiment, a user support event includes a user experience component. A user experience includes the practical, experiential, affective, significant, and/or valuable aspects of human-software interaction including, but not limited to, data entry, question submission, and/or interview process. In one embodiment, a user support event includes a user experience component or components provided or displayed to the user and known to the user support service such as, but not limited to, the following: user interview questions and question sequences, user interfaces, interface displays, sub-displays, images, side bar displays, pop-up displays, alarms, music, backgrounds, avatars, highlighting mechanisms, icons, assistance resources, user recommendations, supplemental actions and recommendations, and/or any other components that individually, or in combination, create a user experience, as discussed herein, and/or as known in the art at the time of filing, and/or as developed after the time of filing.

In one embodiment, a user support event includes a support provider-to-user interaction, e.g. a human-to-human interaction. User support includes a range of services offered to users of a product or products and is intended to help users effectively use the product or products. In various embodiments, a user support event includes asking a question of a user, providing an answer to a user, corresponding with a user, speaking with a user, texting with a user, electronically chatting with a user, and/or registering a complaint from a user. In one embodiment, a user support event may be implemented over a telephone, on live chat, and/or over electronic messages. For example, in one embodiment, the user support event includes a support provider asking a user a question. In one embodiment, the user support event includes a support provider providing an explanation to a user.

In one embodiment, once known user support events are identified at IDENTIFY ONE OR MORE KNOWN USER SUPPORT EVENTS ASSOCIATED WITH PROVIDING SERVICE TO A USER OPERATION 311, process flow proceeds to GENERATE KNOWN USER SUPPORT EVENT DATA OPERATION 313.

In one embodiment, at GENERATE KNOWN USER SUPPORT EVENT DATA OPERATION 313, known user support event data representing the known user support event or events of the monitored one or more user support events associated with providing support to a user is generated.

In one embodiment, the known user support event data of GENERATE KNOWN USER SUPPORT EVENT DATA OPERATION 313 is machine-readable representations of the known user support event.

In one embodiment, once the known user support event data of GENERATE KNOWN USER SUPPORT EVENT DATA OPERATION 313 is generated, process flow proceeds to OBTAIN USER PHYSIOLOGICAL STATUS DATA ASSOCIATED WITH THE USER OPERATION 315.

In one embodiment, at OBTAIN USER PHYSIOLOGICAL STATUS DATA ASSOCIATED WITH THE USER OPERATION 315, current, or relatively current, user physiological status data associated with the user is obtained. According to one embodiment, the user physiological status data associated with the user is obtained using one or more processes, systems, mechanisms, and/or means for obtaining user physiological status data, as discussed herein, as known in the art at the time of filing, and/or as developed after the time of filing.

As a specific illustrative example, in one embodiment, the user physiological status data is obtained using a user physiological status monitoring system. As another specific illustrative example, in one embodiment, the user physiological status data is obtained using a wearable device associated with a user physiological status monitoring system.

In one embodiment, the user physiological status data includes the user's pulse and is obtained using a heart rate monitor operatively coupled to, and/or otherwise associated with, a computing system used to implement at least part of the user physiological status monitoring system. In one embodiment, the user physiological status data includes the user's blood pressure and is obtained using a blood pressure monitor operatively coupled to, and/or otherwise associated with, a computing system used to implement at least part of the user physiological status monitoring system. In one embodiment, the user physiological status data includes the user's facial expression and is obtained using facial expression recognition software and/or hardware operatively coupled to, and/or otherwise associated with, a computing system used to implement at least part of the user physiological status monitoring system. In one embodiment, the user physiological status data includes the user's voice and is obtained using speech recognition software operatively coupled to, and/or otherwise associated with, a computing system used to implement at least part of the user physiological status monitoring system. In one embodiment, the user physiological status data includes the user's body temperature and is obtained using a temperature sensor operatively coupled to, and/or otherwise associated with, a computing system used to implement at least part of the user physiological status monitoring system. In one embodiment, the user physiological status data includes data measuring the user's perspiration and is obtained using a perspiration sensor operatively coupled to, and/or otherwise associated with, a computing system used to implement at least part of the user physiological status monitoring system. In one embodiment, the user physiological status data includes the force with which the user interacts with hardware associated with the user physiological status monitoring system and is obtained using a pressure sensor associated with a keyboard, and/or mouse, touch screen, and/or other user interface system operatively coupled to, and/or otherwise associated with, a computing system used to implement at least part of the user physiological status monitoring system. In one embodiment, the user physiological status data includes the speed with which the user interacts with hardware associated with the user physiological status monitoring system and is obtained using a sensor associated with a keyboard and/or mouse, touch screen, and/or other user interface system operatively coupled to, and/or otherwise associated with, a computing system used to implement at least part of the user physiological status monitoring system.

Numerous means, methods, systems, algorithms, procedures, and processes are known in the art for obtaining user physiological status data associated with a user. Consequently, a more detailed discussion of any particular means, method, system, algorithm, procedure, and process for obtaining user physiological status data associated with a user is omitted here to avoid detracting from the invention.

In one embodiment, once user physiological status data associated with the user is obtained at OBTAIN USER PHYSIOLOGICAL STATUS DATA ASSOCIATED WITH THE USER OPERATION 315, process flow proceeds to ANALYZE AND/OR COMPARE THE OBTAINED USER PHYSIOLOGICAL STATUS DATA AND THE THRESHOLD PARAMETER DATA ASSOCIATED WITH THE ONE OR MORE TYPES OF USER PHYSIOLOGICAL STATUS DATA OPERATION 317

In one embodiment, at ANALYZE AND/OR COMPARE THE OBTAINED USER PHYSIOLOGICAL STATUS DATA AND THE THRESHOLD PARAMETER DATA ASSOCIATED WITH THE ONE OR MORE TYPES OF USER PHYSIOLOGICAL STATUS DATA OPERATION 317, the obtained user physiological data and the threshold parameter data associated with the one or more types of user physiological status data are analyzed and/or compared.

In one embodiment, once the obtained user physiological status data and the threshold parameter data associated with the one or more types of user physiological status data, are analyzed and/or compared at ANALYZE AND/OR COMPARE THE OBTAINED USER PHYSIOLOGICAL STATUS DATA AND THE THRESHOLD PARAMETER DATA ASSOCIATED WITH THE ONE OR MORE TYPES OF USER PHYSIOLOGICAL STATUS DATA OPERATION 317, process flow proceeds to BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319.

In one embodiment, at BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319, it is determined whether the user would benefit from intervention based at least in part on the analysis of the obtained user physiological status data, the threshold parameter data associated with the one or more types of obtained user physiological status data, and the known user support event data.

In various embodiments, at BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319, whether it is determined that the user would benefit from intervention is based upon analysis of one or more of the known user support event data, the threshold parameter data, and the obtained user physiological status data. In various embodiments, the user physiological status data includes, but is not limited to, the user's heart rate, the user's blood pressure, the volume of the user's voice, the speed with which the user is speaking, the frequency of the user voice, changes in the frequency of the user's voice, the cadence with which the user is speaking, the user's body temperature, whether the user is perspiring, the amount of perspiration present on the user's skin, the force with which the user interacts with hardware associated with the user physiological status monitoring system, the speed with which the user interacts with hardware associated with the user physiological status monitoring system, and/or various other user physiological status data similar to the specific illustrative user data examples discussed herein.

In one embodiment, whether it is determined that the user would benefit from intervention is based on analysis of user physiological status data such as, but not limited to, historical user data representing the individual user's historical data and experiences related to the known user support event being experienced by the user. In one embodiment, whether it is determined that the user would benefit from intervention is based on user physiological status data such as, but not limited to, data related to the known user support event being experienced by the user and associated with a segment of users having characteristics comparable to the user.

In one embodiment, the obtained user physiological status and threshold parameter data associated with the one or more types of user physiological status data are analyzed. In one embodiment, the user physiological status data associated with the user is analyzed and/or compared to the threshold parameter data associated with the type of user physiological status data received.

In one embodiment, based at least in part on the analysis of the obtained user physiological status data and the threshold parameter data associated with the one or more types of obtained user physiological status data, it is determined whether the user is in an emotional state such that the user would benefit from intervention.

The emotional state of a user can include, but is not limited to, the following: a stressed emotional state; an upset emotional state; a frustrated emotional state; a happy emotional state or happiness; a sad emotional state or sadness; a surprised emotional state or surprise; a fearful emotional state or fear; a disgusted emotional state or disgust; an angry emotional state or anger; a tense emotional state; a nervous emotional state; a depressed emotional state; a bored emotional state; a fatigued emotional state; an alert emotional state; an excited emotional state; an elated emotional state; a contented emotional state; a serene emotional state; a relaxed emotional state; and/or a calm emotional state.

For example, if the user's physiological status data shows that the user's heart is beating at a rate of 110 beats per minute and the defined threshold parameter data provides that when a user's heart is beating a rate greater than 100 beats per minute, the user is stressed, the user physiological status data and the threshold parameter data is analyzed and a determination is made that the user would benefit from intervention. In one embodiment, when it is determined that the user would benefit from intervention, an intervention notification is sent to the support provider.

In one embodiment, once it is determined whether the user would benefit from intervention at BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319, process flow proceeds to WOULD USER BENEFIT FROM INTERVENTION? OPERATION 321.

In one embodiment, if the user would benefit from intervention at BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319, process flow proceeds to PROVIDE INTERVENTION NOTICE TO USER SUPPORT SERVICE 323.

In one embodiment, at PROVIDE INTERVENTION NOTICE TO USER SUPPORT SERVICE 323, an intervention notice is provided to the support provider.

For example, many call centers have institutional knowledge about which call center workers are particularly adept at assisting frustrated customers. In traditional user support services, once a call center worker realizes that she is speaking with an angry customer, she may transfer the customer to one of these particularly adept workers. In the present disclosure, in one embodiment, at ANALYZE AND/OR COMPARE THE OBTAINED USER PHYSIOLOGICAL STATUS DATA AND THE THRESHOLD PARAMETER DATA ASSOCIATED WITH THE ONE OR MORE TYPES OF USER PHYSIOLOGICAL STATUS DATA OPERATION 317, a user's physiological status data is analyzed before the user speaks with a call center worker. If, at BASED, AT LEAST IN PART, ON THE ANALYSIS OF THE OBTAINED USER PHYSIOLOGICAL STATUS DATA, THE THRESHOLD PARAMETER DATA ASSOCIATED WITH THE ONE OR MORE TYPES OF OBTAINED USER PHYSIOLOGICAL STATUS DATA, AND THE KNOWN USER SUPPORT EVENT DATA, DETERMINE WHETHER THE USER WOULD BENEFIT FROM INTERVENTION OPERATION 319, it is determined that the user is in an emotional state that requires intervention, an intervention notice is provided to the call center at PROVIDE INTERVENTION NOTICE TO USER SUPPORT SERVICE 323. In one embodiment, the intervention notice serves to direct the user to a particularly adept call center worker. Thus, in one embodiment, directing the user to the particularly adept call center worker is an intervention.

In one embodiment, at PROVIDE INTERVENTION NOTICE TO USER SUPPORT SERVICE 323, when the intervention notice is provided to the support provider, process 300 then returns to MONITOR ONE OR MORE KNOWN USER SUPPORT EVENTS ASSOCIATED WITH PROVIDING SERVICE TO A USER 311 and operations 311, 313, 315, 317, 319, 321, and 323 are repeated or looped such that the known user support event and user physiological status data are periodically monitored until the user is determined to be in an emotional state that does not require intervention. In one embodiment, operations 311, 313, 315, 317, 319, 321, and 323 are repeated or looped such that the known user support event and user physiological status data are relatively continually monitored until the user is determined to be in an emotional state that does not require intervention. In one embodiment, once the user is determined to be in an emotional state that does not require intervention, process flow proceeds to EXIT OPERATION 330.

In one embodiment, at WOULD USER BENEFIT FROM INTERVENTION? OPERATION 321, when it is determined that the user would not benefit from intervention, process flow proceeds to EXIT OPERATION 330.

In one embodiment, at EXIT OPERATION 330 process 300 for using physiological status data to determine whether a user would benefit from user support intervention is exited to await new data.

The various embodiments of process 300 for using physiological status data to determine whether a user would benefit from user support intervention improve the technical fields of customer service, customer support, communications, and data processing by ensuring that users who are in need of or would benefit from user support services receive a support intervention. Therefore, implementations of embodiments of process 300 for using physiological status data to determine whether a user would benefit from user support intervention also represent a significant improvement to the field of user experience, particularly by allowing for the more efficient allocation of human and non-human resources. For example, by providing additional or different user support to users who would benefit from an intervention, user support services allocate resources to the users who would benefit most.

In addition, by user support interventions to only those users who are in need of or would benefit from an intervention, process 300 for using physiological status data to determine whether a user would benefit from user support intervention allows for fewer processor cycles being utilized, reduced memory utilization, and less communications bandwidth being utilized to relay data to and from user computing systems. As a result, computing systems are transformed into faster, more efficient, and more effective computing systems by implementing the embodiments disclosed herein of process 300 for using physiological status data to determine whether a user would benefit from user support intervention.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Unless specifically stated otherwise, as would be apparent from the above discussion, it is appreciated that throughout the above description, discussions utilizing terms such as "accessing," "analyzing," "obtaining," "identifying," "associating," "aggregating," "initiating," "collecting," "creating," "defining," "transferring," "generating," "obtaining," "generating," "determining," "defining," "storing," "searching," "comparing," "providing," "processing" etc., refer to the action and processes of a computing system or similar electronic device that manipulates and operates on data represented as physical (electronic) quantities within the computing system memories, resisters, caches or other information storage, transmission or display devices.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes by a computer program stored via a computer program product as defined herein that can be accessed by a computing system or other device to transform the computing system or other device into a specifically and specially programmed computing system or other device.

Those of skill in the art will readily recognize that the algorithms and operations presented herein are not inherently related to any particular computing system, computer architecture, computer or industry standard, or any other specific apparatus. It may prove efficient to construct or transform one or more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity, and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

In the discussion above, certain aspects of one embodiment include process steps and/or operations and/or instructions described herein for illustrative purposes in a particular order and/or grouping. However, the particular order and/or grouping shown and discussed herein is illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Therefore, numerous variations, whether explicitly provided for by the specification or implied by the specification or not, may be implemented by one of skill in the art in view of this disclosure.

What is claimed is:

1. A method for using physiological status data to determine whether a user would benefit from user support intervention comprising:
    defining one or more types of user physiological status data to be obtained and analyzed;
    defining threshold parameters for the defined one or more types of user physiological status data to be obtained and analyzed;
    generating threshold parameter data representing the defined threshold parameters for the defined one or more types of user physiological status data to be obtained and analyzed;
    storing the threshold parameter data in a partitioned threshold parameter data section of a memory device and/or system;
    monitoring one or more user support events associated with providing support to a user, the monitored user support event being a human-software interaction being undertaken by the user, the human-software interaction including a data entry event being performed by the user;
    generating known user support event data;
    obtaining user physiological status data associated with the user, the obtained user physiological status data being one or more of the defined one or more types of user physiological status data, the obtained user physiological status data including data acquired from measuring the user's eye rotation;
    analyzing the obtained user physiological status data, the threshold parameter data associated with the one or more types of obtained user physiological status data, and the known user support event data;
    determining, based at least in part on the analysis of the obtained user physiological status data, the threshold parameter data associated with the one or more types of obtained user physiological status data, and the known user support event data, whether the user would benefit from intervention; and
    providing, upon a determination that the user would benefit from intervention, an intervention notice to a user support service.

2. The method for using physiological status data to determine whether a user would benefit from user support intervention of claim 1, wherein the user physiological status data is obtained via at least one or more of the following:
    a wearable computing system;
    a server computing system;
    a workstation;
    a desktop computing system;
    a mobile computing system;
    a database system or storage cluster;
    a virtual asset;
    a hardware system; or
    a communications system.

3. The method for using physiological status data to determine whether a user would benefit from user support intervention of claim 1, wherein the user physiological status data includes one or more of the following:
    data acquired from the user's own characterization of the user's emotional state;

data acquired from the user's own characterization of the user's physical state;
data acquired from historical user data;
data acquired from a segment of users having characteristics comparable to the user;
data acquired from measuring the user's heartbeat;
data acquired from measuring the user's perspiration;
data acquired from measuring the user's respiration;
data acquired from measuring the user's oxygen saturation;
data acquired from measuring the user's blood pressure;
data acquired from measuring the user's skin temperature;
data acquired from measuring the user's muscle tension;
data acquired from measuring the user's neural activity;
data acquired from measuring the user's eye blinking;
data acquired from measuring the user's facial expression;
data acquired from measuring the user's voice and/or speech;
data acquired from measuring the user's skin color and/or changes in the user's skin color; or
data acquired from measuring the user's interactions with hardware associated with a software system.

4. The method for using user physiological status data to determine whether a user would benefit from user support intervention of claim 1, further comprising determining an emotional state of the user based, at least in part, on the analysis of the obtained user physiological status data and the threshold parameter data associated with the one or more types of obtained user physiological status data.

5. The method for using user physiological status data to determine whether a user would benefit from user support intervention of claim 4, wherein the user's emotional state includes at least one or more of the following:
a tense user emotional state;
a nervous user emotional state;
a stressed user emotional state;
an upset user emotional state;
a frustrated user emotional state;
a happy user emotional state or happiness;
a sad user emotional state or sadness;
a surprised user emotional state or surprise;
a fearful user emotional state or fear;
a disgusted user emotional state or disgust;
an angry user emotional state or anger;
a depressed user emotional state;
a bored user emotional state;
a fatigued user emotional state;
an alert user emotional state;
an excited user emotional state;
an elated user emotional state;
a happy user emotional state;
a contented user emotional state;
a serene user emotional state;
a relaxed user emotional state; or
a calm user emotional state.

6. The method for using physiological status data to determine whether a user would benefit from user support intervention of claim 1, wherein the one or more threshold parameters for each defined type of user physiological status data to be obtained and analyzed are defined based on user physiological status data associated with a general population.

7. The method for using physiological status data to determine whether a user would benefit from user support intervention of claim 6, wherein the one or more threshold parameters for each defined type of user physiological status data to be obtained and analyzed includes at least one or more of the following:
a heart rate threshold parameter associated with a user's heartbeat;
a heart rate variability level threshold parameter associated with a user's heartbeat;
a scan path threshold parameter associated with a user's eye rotation;
a fixation period threshold parameter associated with a user's eye rotation;
a skin conductance level threshold parameter associated with a user's perspiration;
a respiration rate threshold parameter associated with a user's respiration;
an oxygen saturation level threshold parameter associated with a user's oxygen saturation;
a blood pressure level threshold parameter associated with a user's blood pressure;
a skin temperature threshold parameter associated with a user's skin temperature;
a muscle tension level threshold parameter associated with a user's muscle tension;
a neural activity level threshold parameter associated with a user's neural activity;
an eye blink rate threshold parameter associated with a user's eye blinking;
a facial muscle movement threshold parameter associated with a user's facial expression;
an acoustic characteristics threshold parameter associated with a user's voice and/or speech;
a contact pressure threshold parameter associated with the user's interactions with hardware associated with a software system; or
a contact rate threshold parameter associated with the user's interactions with hardware associated with a software system.

8. The method for using physiological status data to determine whether a user would benefit from user support intervention of claim 1, wherein the one or more threshold parameters for each defined type of user physiological status data to be obtained and analyzed are customized based on user physiological status profile data associated with a specific user.

9. The method for using physiological status data to determine whether a user would benefit from user support intervention of claim 8, wherein the one or more threshold parameters include at least one or more of the following:
a heart rate threshold parameter associated with the user's heartbeat;
a heart rate variability level threshold parameter associated with the user's heartbeat;
a scan path threshold parameter associated with the user's eye rotation;
a fixation period threshold parameter associated with the user's eye rotation;
a skin conductance level threshold parameter associated with the user's perspiration;
a respiration rate threshold parameter associated with the user's respiration;
an oxygen saturation level threshold parameter associated with the user's oxygen saturation;
a blood pressure level threshold parameter associated with the user's blood pressure;
a skin temperature threshold parameter associated with the user's skin temperature;

a muscle tension level threshold parameter associated with the user's muscle tension;
a physical activity threshold parameter associated with the user's physical activity;
a neural activity level threshold parameter associated with the user's neural activity;
an eye blink rate threshold parameter associated with the user's eye blinking;
a facial muscle movement threshold parameter associated with the user's facial expression;
an acoustic characteristics threshold parameter associated with the user's voice and/or speech;
a contact pressure threshold parameter associated with the user's interactions with hardware associated with a software system;
a user's skin color and/or change in the user's skin color threshold parameter; or
a contact rate threshold parameter associated with the user's interactions with hardware associated with a software system.

10. The method for using physiological status data to determine whether a user would benefit from user support intervention of claim 1, wherein the user support event includes, but is not limited to, at least one or more of the following user support events:
interview questions are presented to the user;
content or topics of the interview questions are presented to the user;
a font size is used while information is presented to the user;
a description length is used while information is presented to the user;
a theme is presented to the user;
an icon type is displayed to the user;
a type of interface format is presented to the user;
an interface display is presented to the user;
an image is displayed to the user;
assistance resources are listed and/or recommended to the user;
user recommendations are presented to the user;
backgrounds are presented to the user;
background audio is presented to the user;
avatars and/or icons are presented to the user;
highlighting mechanisms are used and highlighted components are presented to the user;
support mechanisms are presented to the user; or
supplemental actions and recommendations are presented to the user.

11. The method for using physiological status data to determine whether a user would benefit from user support intervention of claim 1, further comprising intervening on behalf of the user, wherein intervening includes at least one or more of the following intervention mechanisms:
a pop-up display;
a graphic display;
a text message;
an e-mail message;
a phone call or message;
an instant message; or
a printed message.

12. The method for using physiological status data to determine whether a user would benefit from user support intervention of claim 1, wherein the user support service is at least one or more of the following:
a computing system implemented tax preparation software system;
a network accessed tax preparation software system;
a web-based tax preparation software system;
a cloud-based tax preparation software system;
a computing system implemented business management software system;
a network accessed business management software system;
a web-based business management software system;
a cloud-based business management software system;
a computing system implemented accounting software system;
a network accessed accounting software system;
a web-based accounting software system;
a cloud-based accounting software system;
a computing system implemented financial management system;
a network accessed financial management system;
a web-based financial management system; or
a cloud-based financial management system.

13. A computer program product for using physiological status data to determine whether a user would benefit from user support intervention comprising:
a nontransitory computer readable medium; and
computer program code, encoded on the computer readable medium, comprising computer readable instructions which when executed on one or more processors perform a process including:
defining one or more types of user physiological status data to be obtained and analyzed;
defining threshold parameters for the defined one or more types of user physiological status data to be obtained and analyzed;
generating threshold parameter data representing the defined threshold parameters for the defined one or more types of user physiological status data to be obtained and analyzed;
storing the threshold parameter data in a partitioned threshold parameter data section of a memory device and/or system;
monitoring one or more user support events associated with providing support to a user, the monitored user support event being a human-software interaction being undertaken by the user, the human-software interaction including a data entry event being performed by the user;
generating known user support event data;
obtaining user physiological status data associated with the user, the obtained user physiological status data being one or more of the defined one or more types of user physiological status data, the obtained user physiological status data including data acquired from measuring the user's eye rotation;
analyzing the obtained user physiological status data, the threshold parameter data associated with the one or more types of obtained user physiological status data, and the known user support event data;
determining, based at least in part on the analysis of the obtained user physiological status data, the threshold parameter data associated with the one or more types of obtained user physiological status data, and the known user support event data, whether the user would benefit from intervention; and
providing, upon a determination that the user would benefit from intervention, an intervention notice to a user support service.

14. The computer program product for using physiological status data to determine whether a user would benefit from user support intervention of claim 13, wherein the user physiological status data is obtained via at least one or more of the following:
- a wearable computing system;
- a server computing system;
- a workstation;
- a desktop computing system;
- a mobile computing system;
- a database system or storage cluster;
- a virtual asset;
- a hardware system; or
- a communications system.

15. The computer program product for using physiological status data to determine whether a user would benefit from user support intervention of claim 13, wherein the user physiological status data includes one or more of the following:
- data acquired from the user's own characterization of the user's emotional state;
- data acquired from the user's own characterization of the user's physical state;
- data acquired from historical user data;
- data acquired from a segment of users having characteristics comparable to the user;
- data acquired from measuring the user's heartbeat;
- data acquired from measuring the user's perspiration;
- data acquired from measuring the user's respiration;
- data acquired from measuring the user's oxygen saturation;
- data acquired from measuring the user's blood pressure;
- data acquired from measuring the user's skin temperature;
- data acquired from measuring the user's muscle tension;
- data acquired from measuring the user's neural activity;
- data acquired from measuring the user's eye blinking;
- data acquired from measuring the user's facial expression;
- data acquired from measuring the user's voice and/or speech;
- data acquired from measuring the user's skin color and/or changes in the user's skin color; or
- data acquired from measuring the user's interactions with hardware associated with a software system.

16. The computer program product for using physiological status data to determine whether a user would benefit from user support intervention of claim 13, further comprising determining an emotional state of the user based, at least in part, on the analysis of the obtained user physiological status data and the threshold parameter data associated with the one or more types of obtained user physiological status data.

17. The computer program product for using physiological status data to determine whether a user would benefit from user support intervention of claim 16, wherein the user's emotional state includes at least one or more of the following:
- a tense user emotional state;
- a nervous user emotional state;
- a stressed user emotional state;
- an upset user emotional state;
- a frustrated user emotional state;
- a happy user emotional state or happiness;
- a sad user emotional state or sadness;
- a surprised user emotional state or surprise;
- a fearful user emotional state or fear;
- a disgusted user emotional state or disgust;
- an angry user emotional state or anger;
- a depressed user emotional state;
- a bored user emotional state;
- a fatigued user emotional state;
- an alert user emotional state;
- an excited user emotional state;
- an elated user emotional state;
- a happy user emotional state;
- a contented user emotional state;
- a serene user emotional state;
- a relaxed user emotional state; or
- a calm user emotional state.

18. The computer program product for using physiological status data to determine whether a user would benefit from user support intervention of claim 13, wherein the one or more threshold parameters for each defined type of user physiological status data to be obtained and analyzed are defined based on user physiological status data associated with a general population.

19. The computer program product for using physiological status data to determine whether a user would benefit from user support intervention of claim 18, wherein the one or more threshold parameters for each defined type of user physiological status data to be obtained and analyzed includes at least one or more of the following:
- a heart rate threshold parameter associated with a user's heartbeat;
- a heart rate variability level threshold parameter associated with a user's heartbeat;
- a scan path threshold parameter associated with a user's eye rotation;
- a fixation period threshold parameter associated with a user's eye rotation;
- a skin conductance level threshold parameter associated with a user's perspiration;
- a respiration rate threshold parameter associated with a user's respiration;
- an oxygen saturation level threshold parameter associated with a user's oxygen saturation;
- a blood pressure level threshold parameter associated with a user's blood pressure;
- a skin temperature threshold parameter associated with a user's skin temperature;
- a muscle tension level threshold parameter associated with a user's muscle tension;
- a neural activity level threshold parameter associated with a user's neural activity;
- an eye blink rate threshold parameter associated with a user's eye blinking;
- a facial muscle movement threshold parameter associated with a user's facial expression;
- an acoustic characteristics threshold parameter associated with a user's voice and/or speech;
- a contact pressure threshold parameter associated with the user's interactions with hardware associated with a software system; or
- a contact rate threshold parameter associated with the user's interactions with hardware associated with a software system.

20. The computer program product for using physiological status data to determine whether a user would benefit from user support intervention of claim 13, wherein the one or more threshold parameters for each defined type of user physiological status data to be obtained and analyzed are customized based on user physiological status profile data associated with a specific user.

21. The computer program product for using physiological status data to determine whether a user would benefit from user support intervention of claim 20, wherein the one or more threshold parameters include at least one or more of the following:
- a heart rate threshold parameter associated with the user's heartbeat;
- a heart rate variability level threshold parameter associated with the user's heartbeat;
- a scan path threshold parameter associated with the user's eye rotation;
- a fixation period threshold parameter associated with the user's eye rotation;
- a skin conductance level threshold parameter associated with the user's perspiration;
- a respiration rate threshold parameter associated with the user's respiration;
- an oxygen saturation level threshold parameter associated with the user's oxygen saturation;
- a blood pressure level threshold parameter associated with the user's blood pressure;
- a skin temperature threshold parameter associated with the user's skin temperature;
- a muscle tension level threshold parameter associated with the user's muscle tension;
- a physical activity threshold parameter associated with the user's physical activity;
- a neural activity level threshold parameter associated with the user's neural activity;
- an eye blink rate threshold parameter associated with the user's eye blinking;
- a facial muscle movement threshold parameter associated with the user's facial expression;
- an acoustic characteristics threshold parameter associated with the user's voice and/or speech;
- a contact pressure threshold parameter associated with the user's interactions with hardware associated with a software system;
- a user's skin color and/or change in the user's skin color threshold parameter; or
- a contact rate threshold parameter associated with the user's interactions with hardware associated with a software system.

22. The computer program product for using physiological status data to determine whether a user would benefit from user support intervention of claim 13, wherein the user support event includes, but is not limited to, at least one or more of the following user support events:
- interview questions are presented to the user;
- content or topics of the interview questions are presented to the user;
- a font size is used while information is presented to the user;
- a description length is used while information is presented to the user;
- a theme is presented to the user;
- an icon type is displayed to the user;
- a type of interface format is presented to the user;
- an interface display is presented to the user;
- an image is displayed to the user;
- assistance resources are listed and/or recommended to the user;
- user recommendations are presented to the user;
- backgrounds are presented to the user;
- background audio is presented to the user;
- avatars and/or icons are presented to the user;
- highlighting mechanisms are used and highlighted components are presented to the user;
- support mechanisms are presented to the user; or
- supplemental actions and recommendations are presented to the user.

23. The computer program product for using physiological status data to determine whether a user would benefit from user support intervention of claim 13, further comprising intervening on behalf of the user, wherein intervening includes at least one or more of the following intervention mechanisms:
- a pop-up display;
- a graphic display;
- a text message;
- an e-mail message;
- a phone call or message;
- an instant message; or
- a printed message.

24. The computer program product for using physiological status data to determine whether a user would benefit from user support intervention of claim 13, wherein the user support service is at least one or more of the following:
- a computing system implemented tax preparation software system;
- a network accessed tax preparation software system;
- a web-based tax preparation software system;
- a cloud-based tax preparation software system;
- a computing system implemented business management software system;
- a network accessed business management software system;
- a web-based business management software system;
- a cloud-based business management software system;
- a computing system implemented accounting software system;
- a network accessed accounting software system;
- a web-based accounting software system;
- a cloud-based accounting software system;
- a computing system implemented financial management system;
- a network accessed financial management system;
- a web-based financial management system; or
- a cloud-based financial management system.

* * * * *